US012784889B2

(12) United States Patent
Mosaddegh

(10) Patent No.: US 12,784,889 B2
(45) Date of Patent: Nov. 3, 2026

(54) DEVICES FOR TREATMENT OF MEIBOMIAN GLAND DYSFUNCTION WITH MOBILE CONNECTIVITY AND ARTIFICIAL INTELLIGENCE

(71) Applicant: Lillie A. Mosaddegh, San Francisco, CA (US)

(72) Inventor: Lillie A. Mosaddegh, San Francisco, CA (US)

( * ) Notice: Subject to any disclaimer, the term of this patent is extended or adjusted under 35 U.S.C. 154(b) by 0 days.

(21) Appl. No.: 18/990,399

(22) Filed: Dec. 20, 2024

(65) Prior Publication Data

US 2025/0210178 A1 Jun. 26, 2025

Related U.S. Application Data

(60) Provisional application No. 63/612,460, filed on Dec. 20, 2023.

(51) Int. Cl.

| | |
|---|---|
| ***G16H 20/30*** | (2018.01) |
| ***G16H 10/20*** | (2018.01) |
| ***G16H 10/60*** | (2018.01) |
| ***G16H 40/63*** | (2018.01) |
| ***G16H 80/00*** | (2018.01) |

(52) U.S. Cl.

CPC ............. *G16H 20/30* (2018.01); *G16H 10/20* (2018.01); *G16H 10/60* (2018.01); *G16H 40/63* (2018.01); *G16H 80/00* (2018.01)

(58) Field of Classification Search

CPC ........ G16H 10/20; G16H 10/40; G16H 10/60; G16H 10/65; G16H 15/00; G16H 20/10; G16H 20/13; G16H 20/17; G16H 20/30; G16H 20/40; G16H 20/60; G16H 20/70; G16H 20/90; G16H 30/20; G16H 30/40; G16H 40/20; G16H 40/40; G16H 40/60; G16H 40/63; G16H 40/67; G16H 50/20; G16H 50/30; G16H 50/50; G16H 50/70; G16H 50/80; G16H 70/20; G16H 70/40; G16H 70/60; G16H 80/00

See application file for complete search history.

(56) References Cited

U.S. PATENT DOCUMENTS

2021/0350901 A1 * 11/2021 Mason .................... G06F 3/011
2022/0047449 A1 * 2/2022 Zhang .................... A61H 15/02

* cited by examiner

*Primary Examiner* — Chad A Newton
(74) *Attorney, Agent, or Firm* — Sage Patent Group

(57) ABSTRACT

In some examples, a method for providing personalized treatment recommendations for Meibomian Gland Dysfunction (MGD) includes collecting, at a user device comprising one or more processors, sensor data from one or more sensors on a MGD treatment device being used for treatment of a user; supplying, at the user device, the sensor data to a machine learning model trained on training sensor data and training user outcome data; and adjusting, at the user device and based on an output from the machine learning model, one or more treatment parameters for treatment of the user with the MGD treatment device.

20 Claims, 6 Drawing Sheets

DEVICES FOR TREATMENT OF MEIBOMIAN GLAND DYSFUNCTION WITH MOBILE CONNECTIVITY AND ARTIFICIAL INTELLIGENCE

CROSS-REFERENCES TO PRIORITY AND RELATED APPLICATIONS

This application claims the benefit of U.S. Provisional Patent Application No. 63/612,460 filed December 2023 titled "DEVICES FOR TREATMENT OF MEIBOMIAN GLAND DYSFUNCTION WITH MOBILE CONNECTIVITY AND ARTIFICIAL INTELLIGENCE." The entire disclosure of the application recited above is hereby incorporated by reference as if set forth in full in this document, for all purposes.

BACKGROUND

The following relates generally to the treatment of dry eyes and, more specifically, to the application of mechanical pressure for meibomian gland drainage.

The meibomian glands (or tarsal glands) are a type of sebaceous gland inside the substance of the eyelids responsible for the supply of meibum, an oily substance that prevents evaporation of the eye's tear film, Meibum prevents tear spillage onto the cheek, trapping tears between the oiled edge and the eyeball, and makes the closed lids airtight. Dysfunctional meibomian glands often cause city eyes, one of the more common eye conditions. Inflammation of the meibomian glands causes the glands to be obstructed by thick waxy secretions. Besides leading to dry eyes, the obstructions can result in other medical problems. Treatment can include expression of the gland by a professional. In some cases, antibiotics or steroids are prescribed.

SUMMARY

This document describes methods and systems for treatment of meibomian gland dysfunction using artificial intelligence.

The subject matter described herein can be implemented in software in combination with hardware and/or firmware. For example, the subject matter described herein can be implemented in software executed by a processor. In one example implementation, the subject matter described herein may be implemented using a computer readable medium having stored thereon computer executable instructions that when executed by the processor of a computer control the computer to perform steps.

Example computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

DETAILED DESCRIPTION

Figure 1:
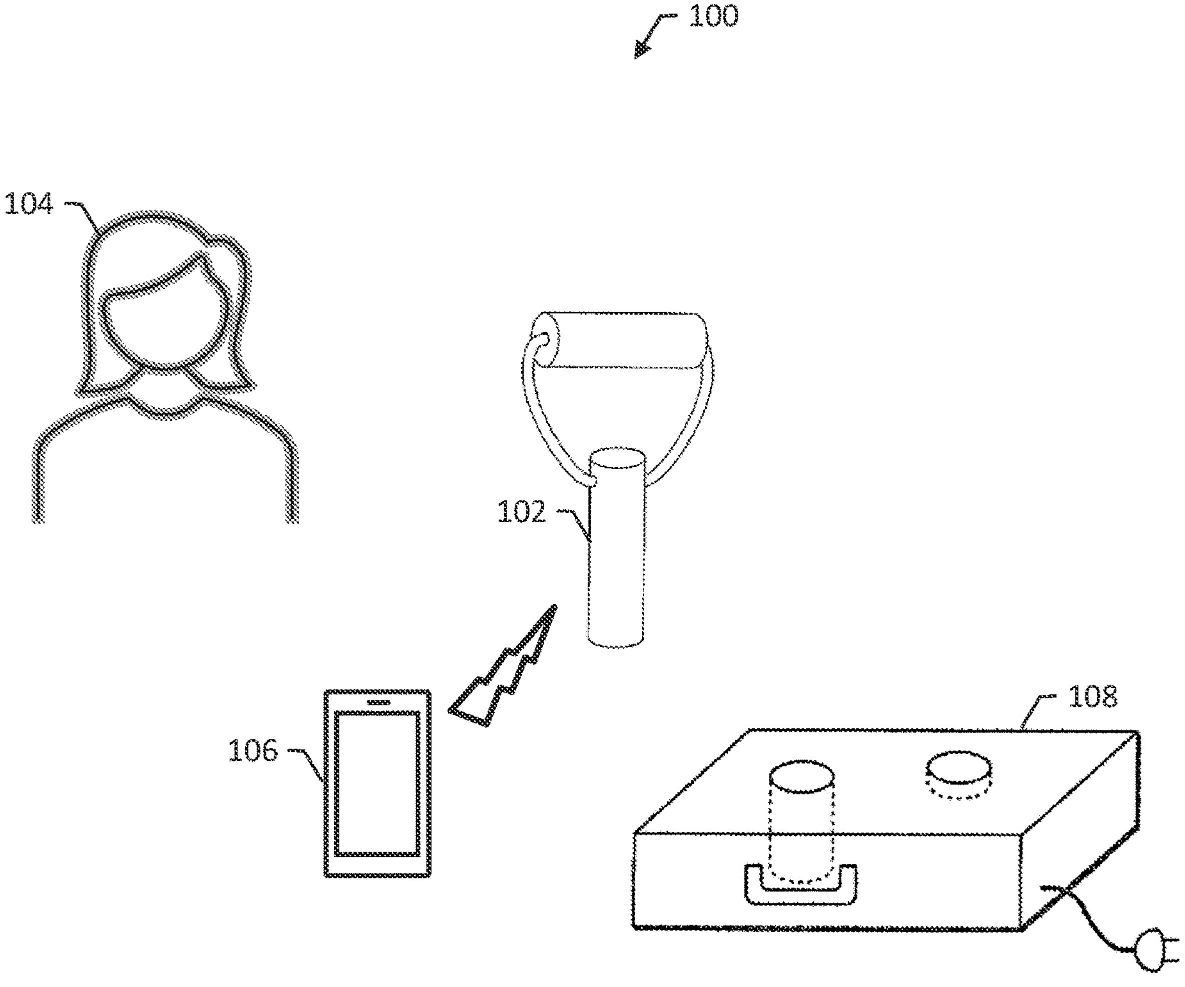
FIG. 1 illustrates an example system for treatment of dry eyes.

The subject matter described herein relates to methods, systems, and computer readable media for using artificial intelligence with meibomian gland rollers and related user devices.

AI integration with an MGD treatment device incorporating a roller can significantly enhance functionality and user experience through various advanced capabilities. For instance, AI can enable predictive maintenance by analyzing sensor data and usage patterns to forecast when the device might require actions such as roller replacement, battery recharging, or cleaning. This reduces downtime and aids consistent performance. Enhanced safety protocols can be implemented through machine learning algorithms capable of detecting unsafe conditions, such as excessive pressure or prolonged use, in real time. The AI can then automatically adjust device parameters or provide warnings to prevent potential harm to the user.

In some examples, AI models can be used for the development of custom treatment plans, where AI uses data from previous treatments and user feedback to tailor therapy parameters, such as roller pressure, treatment duration, or preparatory steps like warming gel pads, to individual needs. AI-driven user engagement features, such as virtual assistants or chatbots, could guide users through treatment sessions while educating them on proper device usage and offering real-time feedback. Furthermore, AI can be configured to analyze trends in user-reported symptoms alongside sensor data to provide insights into treatment efficacy. A computer system can be configured, using AI models, to identify correlations between environmental factors, such as humidity or pollen levels, and symptom severity, offering recommendations for lifestyle adjustments.

In some examples, integration with wearable technology further expands functionality by incorporating data on the user's overall health, such as stress levels or sleep quality, into treatment recommendations. A user device incorporating an AI model can be configured to also facilitate telemedicine by generating detailed treatment reports for remote monitoring and consultation with healthcare providers, enabling more precise adjustments to therapy plans. Real-time feedback during treatment can be enhanced through advanced sensors, such as thermal or optical sensors, allowing AI to assess the quality of meibomian gland oil expression and dynamically adjust device settings for maximum effectiveness.

Environmental data, such as room temperature and air quality, can be included in AI models (e.g., in real time or near real time) to adapt treatment conditions for optimal outcomes. The system can be configured to utilize crowd learning by aggregating anonymized data from multiple devices to identify trends and refine treatment protocols, benefiting all users through collective intelligence. Additionally, AI can be configured to incorporate gamification elements, such as progress tracking with rewards or reminders, to encourage consistent device usage. Augmented or virtual reality applications could further assist users by providing real-time visual guidance on roller positioning to improve treatment accuracy and safety. These capabilities can enhance the device's therapeutic outcomes and also improve usability, personalization, and overall user engagement.

FIG. 1 illustrates an example system 100 for treatment of dry eyes. The system 100 can be used, e.g., at home or outside of the direct supervision of a medical professional.

The system 100 includes a meibomian gland pressure device 102 configured for applying pressure to an eyelid of a user 104, for example, via a roller. The system 100 includes a user device 106 (e.g., mobile phone, tablet, or laptop computer) in communication with the device 102. The system 100 includes an optional base station 108 for the device 102.

The device 102 provides a practical way to self-administer the treatment for one of the leading causes of dry eyes, namely, tear film oil deficiency. The device 102 combines an effective and safe method to use mechanical rolling pressure combined with heat for meibomian gland drainage. The device 102 can be distributed as a kit that is a complete package to melt, effectively and safely milk, and wash away the common hardened contents of a dysfunctional meibomian gland.

The device 102 is designed with an externally-applied roller that can be applied to a closed eye that can be safely used by the consumer on their own eyelids without the need for a clinician inserting anything into the eye. Additionally, the device 102 can have an embedded sensor in the roller to control and maintain the temperature, for example at the range of 42 to 45 degrees Celsius. Since eye shape and size vary from person to person, the roller head width will be designed to be about ⅓ of the width of the average adult person's eyelid size, on the order of 1-2 cm, for example. With this size roller, the device can be used on the eyelid of different size adult eyes, as well as the pediatric population.

The rolling action of this instrument, combined with the rolling head increases its effectiveness in emptying inspissated meibomian glands. The roller tip allows the patient to safely start the application of the pressure at the bottom of the glands and effectively roll open the clogged up oil glands, analogous to squeezing out the contents of a tooth paste tube. The washable roller keeps the head clean for long term use. The removable roller head allows for a multi-user application.

An optional preheated, eye-shaped, soft gel pad can be used to prepare the lids by softening the meibomian gland contents and making it easier for the roller to have a more effective action to induce mechanical extraction of the gland content. A charging well structure can include a well for heating the eye-shaped gel pad. This allows for pads to be heated without use of a microwave to heat the gel pad, which makes it safer as well as more convenient to use.

This can be safer, for example, because no microwaves are used to heat up the gel before its application so close to the eye. It is more convenient since it can be used at any location simply by plugging it into an electric outlet or using the rechargeable battery. The gel pad can be designed to maintain the temperature between, for example, 42 and 45 degrees Celsius for 3 to 5 minutes or longer.

Figure 2A:
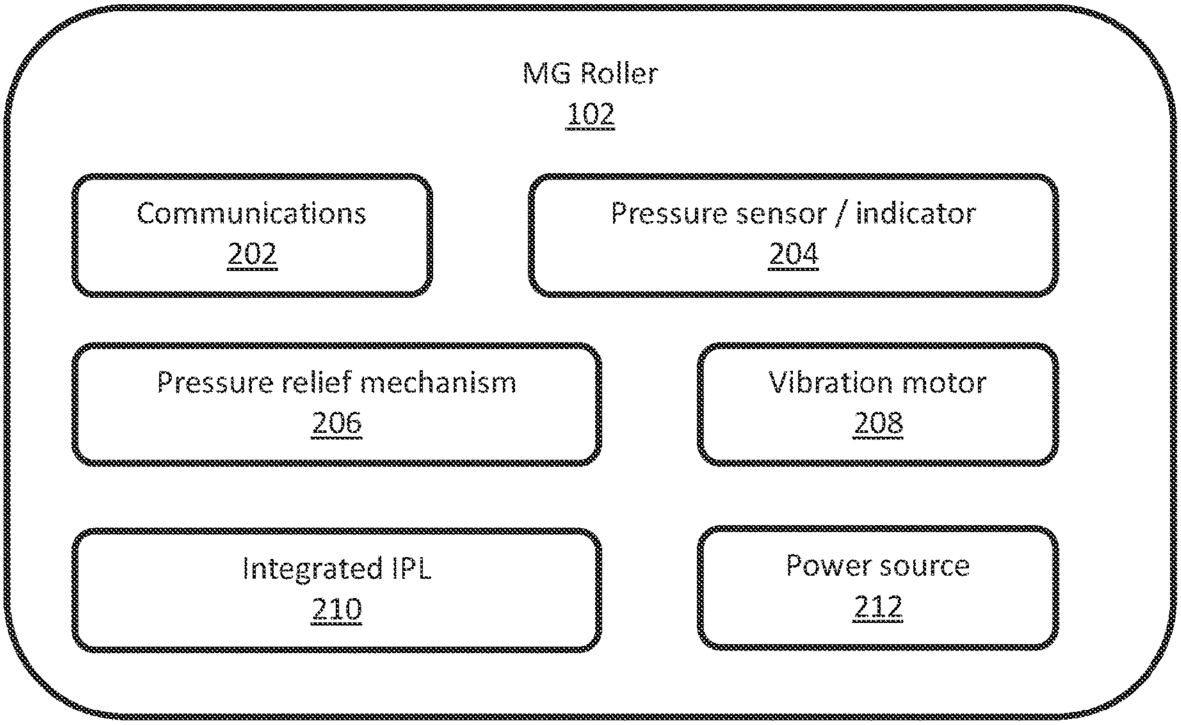
FIG. 2A is a block diagram of an example device.

FIG. 2A is a block diagram of an example device 102. The device 102 can include a communications circuit 202, e.g., a wireless circuit having an antenna, configured for communicating with the user device 106. For example, the device 102 can send sensor data to the user device 106 and receive control instructions from the user device 106. The communications circuit 202 can be a Bluetooth module. The device 102 includes a power source 212, for example, an integrated rechargeable battery allowing for portable use.

The device 102 can include a pressure sensor and/or a pressure indicator 204. For example, the device 102 can include a strain gauge, load cell, or piezoelectric pressure sensor configured for measuring a pressure applied by a user. The roller can include a pressure indicator such as a vibration motor 208 and/or an audio speaker configured to produce an audio chirp if the pressure exceeds a threshold.

The device 102 can include a pressure relief mechanism 206 for automatically relieving pressure in the case of the user applying pressure greater than a threshold. For example, the device 102 can include a clamp assembly configured to release the roller from one or more arms in response to overpressure.

In some examples, the device 102 includes an integrated intense pulsed light (IPL) therapy system 210 configured for producing pulsed light. For example, the device 102 can include a light emitting diode configured for producing the pulsed light.

In general, the device 102 can include any appropriate type of sensors. FIG. 2A shows that the device 102 may include one or more other sensors 214, for example, temperature sensors, optical sensors, and oil flow rate sensors.

There are a few different types of sensors that could be used to detect the oil flow rate an eye of a patient. One type is a microfluidic sensor. This type of sensor uses small channels and chambers to control the flow of fluids. Microfluidic sensors are very sensitive and can be used to measure very small flow rates.

Another type of sensor that could be used is a thermal sensor. This type of sensor measures the temperature of a fluid. When oil flows, it generates heat. By measuring the temperature of the oil, a thermal sensor can be used to measure the flow rate.

Moreover, a fiber optic sensor could also be used to measure oil flow rate. This type of sensor uses light to measure the flow of fluids. Fiber optic sensors are very small and can be inserted into the eye without causing any damage.

Figure 2B:
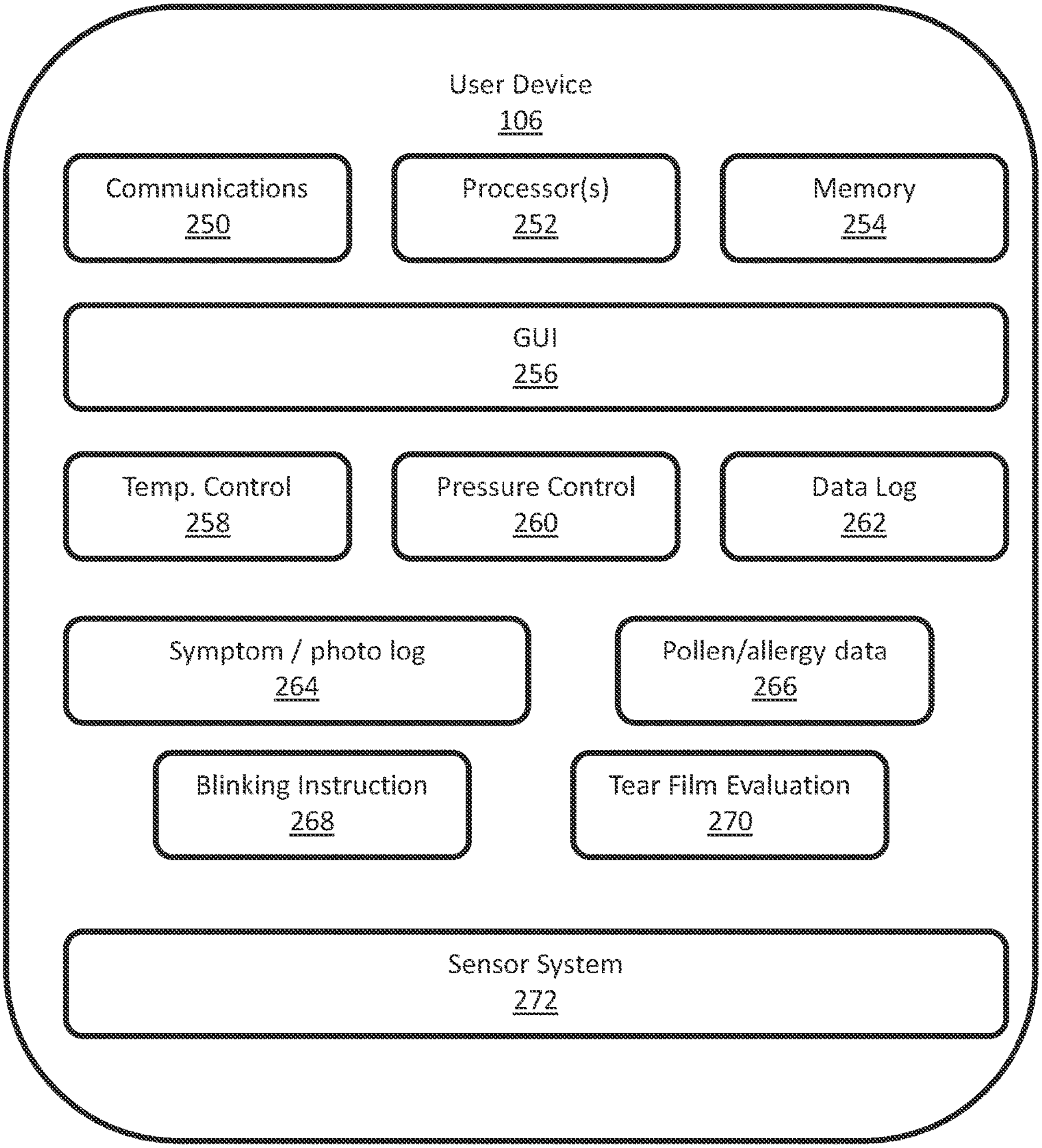
FIG. 2B is a block diagram of an example user device, e.g., a phone, tablet, laptop, or other suitable computing device.

FIG. 2B is a block diagram of an example user device 106, e.g., a phone, tablet, laptop, or other suitable computing device. The user device 106 includes a communications circuit 250 for communicating with the roller 102 (for example, a Bluetooth module), one or more processors 252, and memory storing instructions for the processors 252.

In operation, the user device 106 can use machine learning to determine treatment parameters for a patient, providing a therapeutic experience. The user device 106 can be used for collecting, for example, real-time data and time lapse data. The user device 106 can use machine learning models to analyze data from the device 102, provide feedback to a user, and adjust device parameters for a treatment program. The user device 106 can use real-time data and historic data, e.g., statistical data from a centralized database.

The user device 106 includes a graphical user interface (GUI) 256 that allows the user 104 to interact with the user device 106. The GUI 256 can display, e.g., recorded data, operational instructions, and control elements. The GUI 256 can show the user, for example, how to start and stop the device 102, adjust the intensity of the stimulation, and track their progress over time.

For example, the GUI 256 can include an intensity slider to allow the user to adjust the intensity of stimulation to the eyelid. The intensity should be adjustable from very light to very strong, so that the user can find a setting that is comfortable and effective for them. In another example, the GUI 256 can include a progress tracker to show the user how much time they have spent using the device 102 and how many times they have used it. This information can help the user to track their progress and see how the device is helping them.

The user device 106 includes a temperature control module 258, an overpressure control module 260, and a data logger 262 configured for recording sensor data form the roller 102 with timestamps. The user device 106 includes a symptom and/or photo log 264 with timestamps and pollen/allergy data 266 with time stamps.

The user device 106 can provide instructions 268 for blinking exercises. In some examples, the user device 106 performs tear film evaluation using a camera of the device 106. In some examples, the user device 106 includes a sensor system 272, for example, including a camera and possibly other sensors or devices configured for collecting feedback.

The user device 106 can include additional optional features such as:

- Reminders: The app could send reminders to the user to use the device 102 at regular intervals. This can help the user to stay on track with their treatment.
- Custom schedules: The app could allow the user to create custom schedules for using the device 102. This can be useful for users who have specific needs, such as using the device 102 before work or before going to bed.
- Data tracking: The app could track the user's progress over time and provide reports. These reports can be helpful for the user to see how the device 102 is helping them and to identify any areas where they need to improve.
- Integration with other health apps: The app could integrate with other health apps, such as a sleep tracker or a fitness tracker. This would allow the user to see how their tear duct activity is related to other aspects of their health.

The software functionality of the user device 106 can be implemented in a cloud-based system, where some or all the functions of the user device 106 are executed on a remote computer system. The user device 106 then communicates with the remote computer system, for example, over a data communications network such as the Internet.

The user device 106 can use one or more machine learning models to adjust treatment parameters based on sensor data. Treatment parameters can include, for example, temperature, massage intensity, and duration. Treatment parameters can include guidance for additional procedures, for example, lid rinse or other cleaning procedures.

In some examples, the user device 106 is configured to automatically perform maintenance or perform automatic notification of maintenance tasks for the device 102. The user device 106 can monitor the health of the device 102 and performance metrics and, for example, determine when a component is likely to fail or when the battery might degrade beyond a useful threshold. The user device 106 can alert users in advance about possible maintenance tasks, to better ensure uninterrupted treatment.

Figure 3:
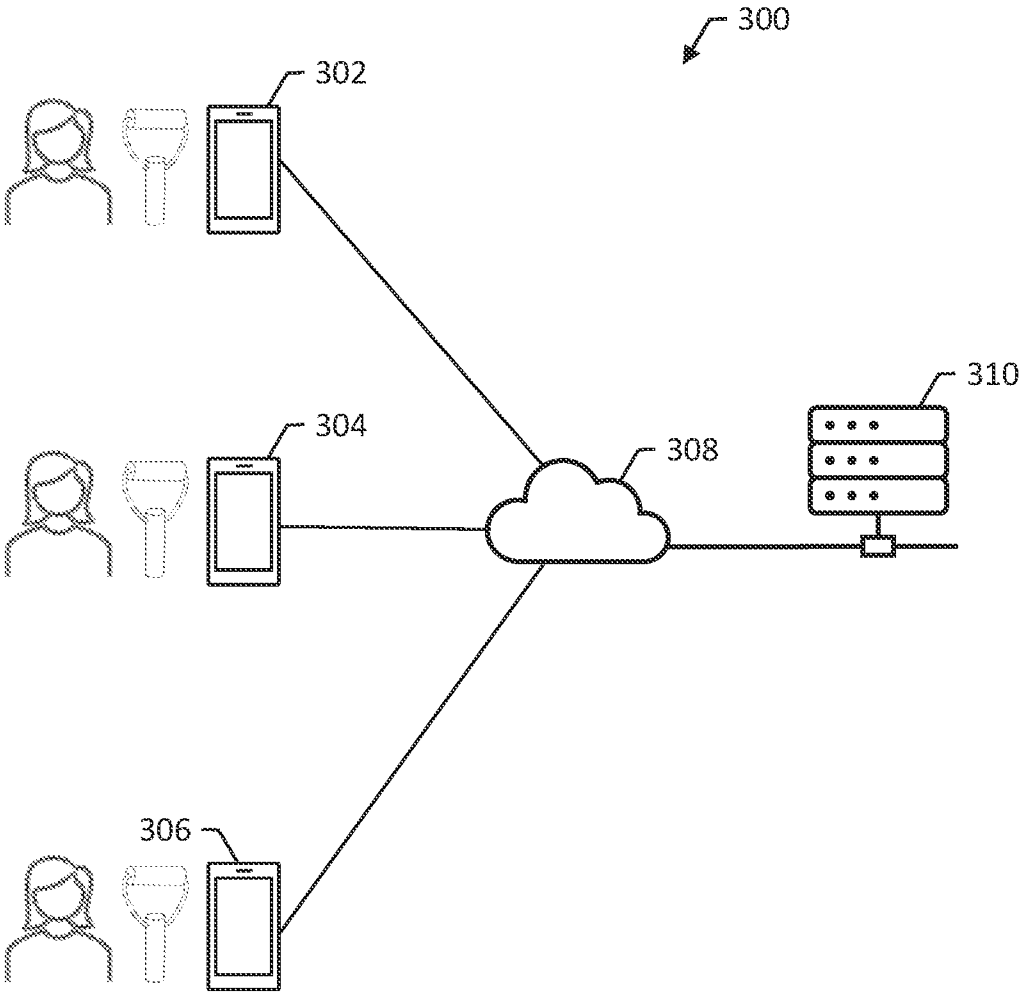
FIG. 3 is a block diagram of an example system for collecting training data and training AI models for the device.

FIG. 3 is a block diagram of an example system 300 for collecting training data and training AI models for the device 102. The system 300 includes multiple user devices 302, 304, and 306 each communicating over a data communications network 308 (e.g., the Internet) with a central server 310 configured for receiving training data, training AI models, and distributing the AI models to the user devices 302, 304, and 306.

In general, the system 300 collects training data such as sensor data, user feedback data, and treatment parameters. The system 300 trains one or more AI models to receive input data (for example, sensor data and treatment parameters) and output treatment parameters configured to improve user outcomes (for example, as determined by user feedback or sensor data or, in some cases, even feedback from medical professionals).

The system 300 can analyze data to discern, e.g., patterns, trends, or correlations between treatment parameters and treatment outcomes. Based on the analysis, the system 300 generates AI models configured to adjust and recommend treatment parameters for individual users, targeting increased efficiency and comfort.

The user devices 302, 304, and 306 can use adaptive learning to continue to improve the models over time as additional training data and/or sensor data is collected. For example, the user devices 302, 304, and 306 can adapt to the changing needs of the users, such as if their MGD symptoms change in severity or scope.

The system 300 can be configured to create models for one or more of the following features:

User Engagement and Feedback Loop
- An AI-driven chatbot in the mobile application can communicate with users, collecting feedback, answering questions, and guiding them through the treatment process.
- Based on this feedback, the AI can further refine its treatment suggestions or offer additional educational content tailored to the user's needs.

Remote Monitoring and Telemedicine Integration
- The AI can analyze and present data in a structured manner, which can be shared with healthcare providers while preserving patient privacy in accordance with laws and regulations.
- In cases where the user's condition worsens or doesn't improve as expected, the AI can recommend scheduling a consultation with a specialist.
  - Dr recommendation with referral network Trend Analysis and Reporting
- The AI can provide insights into how a user's condition is progressing over time.
- This long-term data can be beneficial for users and their healthcare providers, giving a clearer picture of the disease's progression and the treatment's effectiveness.

Safety Protocols
- AI can monitor the device in real-time and initiate safety protocols if anomalies like overheating or excessive pressure are detected.
- It can also alert users to take breaks if it determines that continuous usage might be harmful.

Integration with Other Health Data
- The AI can be integrated with other health monitoring apps or devices. By analyzing additional data like sleep patterns, diet, or stress levels, the AI might offer insights into how these factors correlate with MGD or its treatment effectiveness.
  - Apple® health
  - Fitness and health devices, for example, Oura devices User Training and Onboarding
- The AI can guide new users through the device setup and initial treatment sessions, making the onboarding process smoother.

It can use augmented reality (AR) features on the phone to provide real-time guidance, showing users exactly how to use the device correctly.

Continuous Updates

As research on MGD progresses and new findings emerge, the AI algorithms can be updated accordingly. Users can benefit from the latest research without needing to purchase a new device.

Integrating artificial intelligence into the MGD treatment device offers numerous potential benefits. From personalized treatment protocols and safety enhancements to integration with telemedicine and continuous learning, AI can significantly improve the device's efficiency, user-friendliness, and overall efficacy.

Collective Database can Support Research

Figure 4:
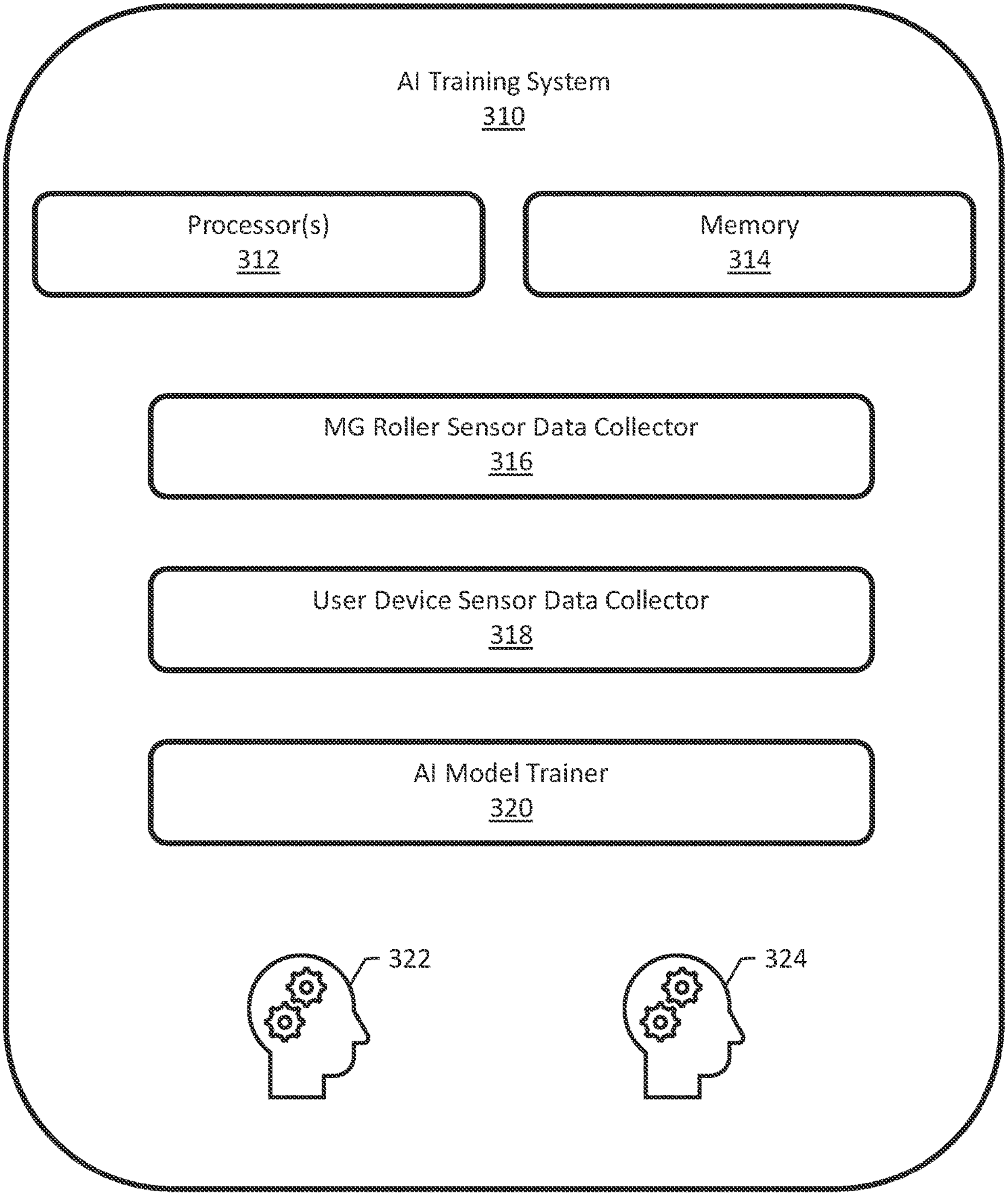
FIG. 4 is a block diagram of an example AI training system implemented on one or more processors and memory storing instructions for the processors.

FIG. 4 is a block diagram of an example AI training system 310 implemented on one or more processors 312 and memory 314 storing instructions for the processors 312. The training system 310 includes a roller sensor data collector 316, a user device sensor data collector 318, and an AI model trainer 320 for generating a first AI model 322 for the roller sensor data and a second AI model 324 for the user device sensor data.

The roller sensor data collector 316 is a software component configured to acquire and preprocess sensor data from the MGD treatment device. The roller sensor data collector 316 can be configured to interface with various sensors embedded in the MGD treatment device, including pressure sensors, temperature sensors, and oil flow rate sensors, to gather data in real-time during the treatment process. The collected data can, in some cases, include key operational metrics such as the pressure applied by the roller, the temperature maintained during treatment, and the flow characteristics of meibomian gland oil. By continuously monitoring these parameters, the roller sensor data collector 316 can be configured to aid in ensuring that the treatment adheres to predefined safety thresholds and therapeutic guidelines.

In some examples, the roller sensor data collector 316 also supports advanced data management features, such as filtering and error correction, to ensure the integrity and reliability of the sensor inputs. For example, the roller sensor data collector 316 can be configured to implement algorithms to detect anomalies, such as abrupt pressure spikes or temperature deviations, and can trigger alerts or safety protocols in response. Additionally, the roller sensor data collector formats and timestamps the data, preparing it for subsequent analysis by the AI model trainer 320. This preprocessing step allows the AI system to focus on generating accurate and actionable insights rather than compensating for raw data inconsistencies.

In some examples, to facilitate adaptive treatment protocols, the roller sensor data collector 316 supports real-time data transmission to the user device via a wireless communication module, such as Bluetooth. This connectivity enables the seamless integration of user feedback and sensor inputs into a unified data pipeline, forming the foundation for dynamic adjustments to treatment parameters. By serving as the primary interface between the MGD treatment device and the AI training system, the roller sensor data collector plays a pivotal role in enabling personalized, data-driven therapeutic solutions.

The user device sensor data collector 316 is a software component configured for gathering data from the sensors integrated into the user device, such as a mobile phone, tablet, or laptop, during the operation of the MGD treatment system. These sensors may include cameras for capturing high-resolution images or video of the eye, ambient temperature sensors, accelerometers, and potentially other physiological or environmental monitoring tools. The data collected by this component complements the information provided by the MGD treatment device, offering a broader context for analyzing treatment effectiveness and user engagement.

The user device sensor data collector 318 can be configured to process visual data captured by the camera, such as images of the eyelid before, during, and after treatment. These images can be used to evaluate tear film quality, gland expression results, or signs of inflammation. The collector may apply image preprocessing techniques, such as noise reduction, normalization, or feature extraction, to enhance the quality of the input data for the AI model trainer 320. Similarly, ambient temperature readings are analyzed to assess external conditions that might influence treatment outcomes, while accelerometer data can track device usage patterns or detect potential misuse.

The user device sensor data collector 318 can be configured to integrate its data with the roller sensor data to build a comprehensive dataset for training and inferencing by the AI system. By correlating user device data with treatment device sensor readings, the system can better understand the relationship between user behavior, environmental factors, and treatment efficacy. Additionally, the user device sensor data collector ensures data integrity through timestamping and synchronization mechanisms, enabling consistent and accurate temporal alignment with the roller sensor data. Through its robust data collection and processing capabilities, the user device sensor data collector 318 significantly enhances the AI-driven personalization and adaptability of the MGD treatment system.

The AI model trainer 320 is software module designed to generate, refine, and validate machine learning models for the MGD treatment system. The AI model trainer 320 processes sensor data collected by the roller sensor data collector 316 and the user device sensor data collector 318 to identify patterns and correlations that inform treatment protocols. By leveraging supervised and unsupervised learning techniques, the AI model trainer 320 can analyze vast amounts of data, encompassing user feedback, device sensor readings, and environmental variables, to develop models that optimize treatment outcomes.

In some examples, the AI model trainer 320 operates in a distributed architecture, enabling it to aggregate data from multiple devices and users through a centralized server. This aggregated dataset allows the system to capture a diverse range of usage scenarios and physiological responses, improving the generalizability and robustness of the trained models. The trainer employs advanced machine learning algorithms, such as neural networks or ensemble methods, to produce models that predict optimal treatment parameters, including roller pressure, temperature, and duration, tailored to individual users.

Some key features of the AI model trainer 320 may include iterative training and validation processes to ensure the accuracy and reliability of the models. The AI model trainer 320 can split the data into training, validation, and testing subsets, allowing it to continuously evaluate model performance and fine-tune hyperparameters for improved accuracy. Additionally, the trainer supports adaptive learning, incorporating new data over time to refine the models in response to changing user needs or updated medical guidelines.

Once the models are trained, the AI model trainer 320 deploys them to user devices for real-time inferencing. This deployment enables the system to make personalized adjustments to treatment protocols on the fly, such as increasing roller pressure or extending treatment duration based on sensor feedback and historical trends. The AI model trainer 320 also facilitates periodic updates, for example, so that the deployed models remain aligned with the latest advancements in meibomian gland dysfunction treatment and user data. By serving as the central hub for AI model development, the AI model trainer 320 drives the intelligent, data-driven functionality of the MGD treatment system.

Figure 5:
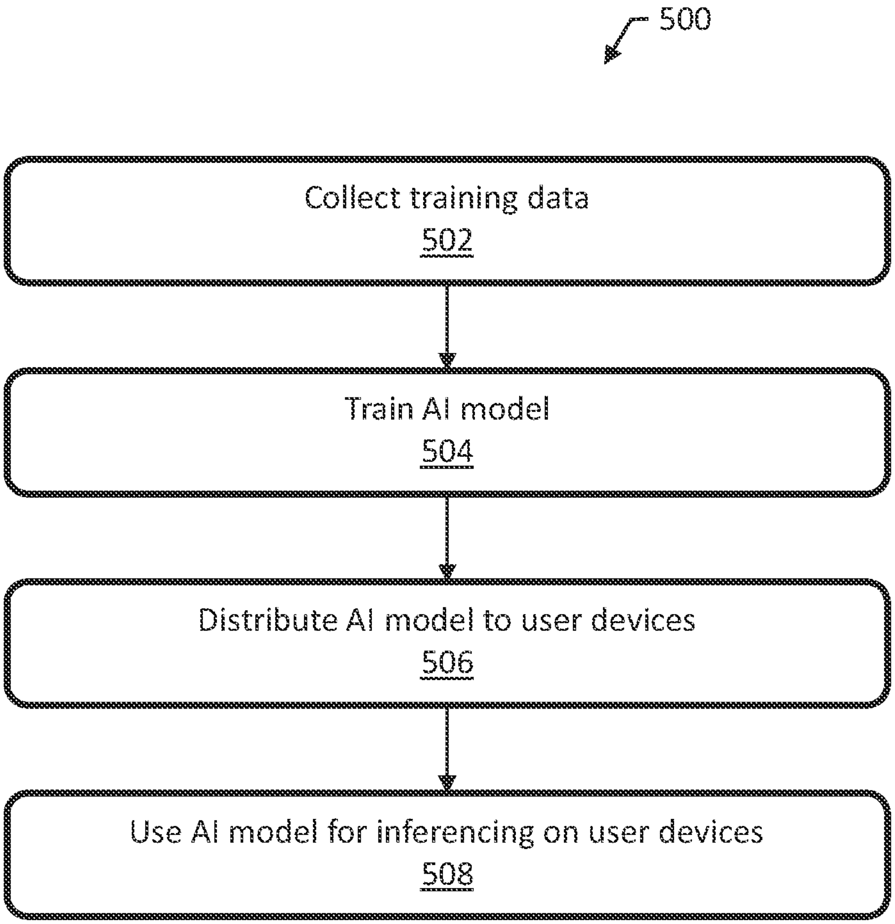
FIG. 5 is a flow diagram of an example method for generating AI models for use with an MG roller.

FIG. 5 is a flow diagram of an example method 500 for generating AI models for use with an MG roller. The method 500 includes collecting training data from user devices (502), training at least one AI model (504), distributing the AI model to the user devices (506), and using the AI model for inferencing on the user devices (508).

Collecting training data from user devices (502) can include gathering sensor data from the MGD treatment devices and associated user devices during their operation. The data includes parameters such as roller pressure, temperature, oil flow rate, eyelid images, and environmental factors. These datasets are preprocessed to remove noise and ensure consistency, enabling the system to build a comprehensive and high-quality foundation for model training. This step also involves synchronizing data from multiple users to create a diverse and representative dataset for generating generalized AI models.

Training at least one AI model (504) can include using the collected training data and machine learning algorithms to generate AI models capable of predicting optimal treatment parameters. This process involves splitting the dataset into training, validation, and testing subsets to iteratively refine the models and assess their accuracy. Advanced techniques, such as deep learning and feature extraction, may be utilized to capture complex patterns and correlations in the data. The resulting AI models are tuned to optimize metrics such as treatment efficacy, user comfort, and safety thresholds.

Distributing the AI model to the user devices (506) can include deployment via a secure network. The distribution process is configured such that the models are compatible with the hardware and software configurations of the user devices. By deploying the models locally, the system enables real-time inferencing without the need for continuous internet connectivity, preserving user privacy and enhancing device autonomy. Periodic updates may be pushed to ensure that the models incorporate new insights and remain aligned with evolving medical guidelines.

Using the AI model for inferencing on the user devices (508) can include, at the user device, processing sensor data in real time or near real time to adjust treatment parameters dynamically. For example, it may modify the roller pressure or treatment duration based on feedback from the sensors, ensuring optimal and personalized therapy for the user. The inferencing process is lightweight and designed to operate efficiently on mobile hardware, providing immediate recommendations or adjustments to enhance treatment outcomes. This step closes the feedback loop, leveraging AI to continuously improve the user experience and therapeutic effectiveness.

The scope of the present disclosure includes any feature or combination of features disclosed in this specification (either explicitly or implicitly), or any generalization of features disclosed, whether or not such features or generalizations mitigate any or all of the problems described in this specification. Accordingly, new claims may be formulated during prosecution of this application (or an application claiming priority to this application) to any such combination of features.

In particular, with reference to the appended claims, features from dependent claims may be combined with those of the independent claims and features from respective independent claims may be combined in any appropriate manner and not merely in the specific combinations enumerated in the appended claims.

What is claimed is:

1. A method for providing personalized treatment recommendations for Meibomian Gland Dysfunction (MGD), the method comprising:

collecting, at a user device comprising one or more processors, sensor data from one or more sensors on a MGD treatment device being used for treatment of a user, wherein the MGD treatment device comprises:

a cylinder and an axle, about which the cylinder can rotate, the cylinder configured to roll over and apply pressure to an eyelid of a user, and including a heating element configured to provide controlled thermal energy during treatment;

a handle including a power source;

arms by which the axle is held to the handle and by which power is supplied from the power source to the heating element; and one or more sensors configured to measure at least one of pressure, temperature, or motion of the cylinder during treatment;

supplying, at the user device, the sensor data to a machine learning model trained on training sensor data and training user outcome data; and adjusting, at the user device and based on an output from the machine learning model, one or more treatment parameters for treatment of the user with the MGD treatment device;

wherein machine learning model is configured to receive sensor data collected from the one or more sensors during operation of the MGD treatment device and generate control outputs;

wherein the control outputs dynamically adjust, in real time, the one or more treatment parameters of the MG treatment device during operation, the treatment parameters including at least one of: applied pressure, temperature of the heating element, or rotational speed of the cylinder;

wherein adjusting the one or more treatment parameters comprises operating as a closed-loop control system in which the sensor data is continuously used to update the one or more treatment parameters.

2. The method of claim 1, wherein collecting sensor data comprises collecting additional sensor data from one or more user device sensors on the user device, and wherein supplying the sensor data to the machine learning model comprises supplying the additional sensor data.

3. The method of claim 1, comprising refining one or more treatment suggestions based on accumulated user data.

4. The method of claim 1, comprising adjusting the one or more treatment parameters over time while continuing collecting sensor data.

5. The method of claim 1, comprising collecting, using a graphical user interface of the user device, user feedback from the user and supplying the user feedback to the machine learning model.

6. The method of claim 5, comprising adjusting, the user device, the one or more treatment parameters based on an additional output from the machine learning model based on the user feedback.

7. The method of claim 5, wherein collecting user feedback comprises providing a chatbot configured for collecting feedback, answering user questions, and guiding treatment.

8. The method of claim 1, comprising providing sensor data or user feedback or both to a remote computer system for remote monitoring or telemedicine or both.

9. The method of claim 1, comprising monitoring the MGD treatment device and, in response to the monitoring, initiating one or more safety measures in response to detecting one or more anomalies or unsafe usage patterns.

10. The method of claim 1, comprising analyzing supplementary health data of the user in conjunction with the sensor data or user feedback or both and, in response, adjusting the one or more treatment parameters, wherein the machine learning model is trained using data collected from a plurality of treatment sessions associated with a single user.

11. A system for providing personalized treatment recommendations for Meibomian Gland Dysfunction (MGD), the system comprising:

a MGD treatment device comprising:

a cylinder and an axle, about which the cylinder can rotate, the cylinder configured to roll over and apply pressure to an eyelid of a user, and including a heating element configured to provide controlled thermal energy during treatment;

a handle including a power source;

arms by which the axle is held to the handle and by which power is supplied from the power source to the heating element; and one or more sensors configured to measure at least one of pressure, temperature, or motion of the cylinder during treatment; and a user device comprising one or more processors, wherein the user device is configured for:

collecting sensor data from the one or more sensors while the MGD treatment device is being used for treatment of a user;

supplying the sensor data to a machine learning model trained on training sensor data and training user outcome data; and adjusting, based on an output from the machine learning model, one or more treatment parameters for treatment of the user with the MGD treatment device;

wherein machine learning model is configured to receive sensor data collected from the one or more sensors during operation of the MGD treatment device and generate control outputs;

wherein the control outputs dynamically adjust, in real time, the one or more treatment parameters of the MG treatment device during operation, the treatment parameters including at least one of: applied pressure, temperature of the heating element, or rotational speed of the cylinder;

wherein adjusting the one or more treatment parameters comprises operating as a closed-loop control system in which the sensor data is continuously used to update the one or more treatment parameters.

12. The system of claim 11, wherein collecting sensor data comprises collecting additional sensor data from one or more user device sensors on the user device, and wherein supplying the sensor data to the machine learning model comprises supplying the additional sensor data.

13. The system of claim 11, wherein the user device is configured for refining one or more treatment suggestions based on accumulated user data.

14. The system of claim 11, wherein the user device is configured for adjusting the one or more treatment parameters over time while continuing collecting sensor data.

15. The system of claim 11, wherein the user device is configured for collecting, using a graphical user interface of the user device, user feedback from the user and supplying the user feedback to the machine learning model.

16. The system of claim 15, wherein the user device is configured for adjusting, the user device, the one or more treatment parameters based on an additional output from the machine learning model based on the user feedback.

17. The system of claim 15, wherein collecting user feedback comprises providing a chatbot configured for collecting feedback, answering user questions, and guiding treatment.

18. The system of claim 15, wherein the user device is configured for providing sensor data or user feedback or both to a remote computer system for remote monitoring or telemedicine or both.

19. The system of claim 15, wherein the user device is configured for monitoring the MGD treatment device and, in response to the monitoring, initiating one or more safety measures in response to detecting one or more anomalies or unsafe usage patterns.

20. The system of claim 11, wherein the user device is configured for analyzing supplementary health data of the user in conjunction with the sensor data or user feedback or both and, in response, adjusting the one or more treatment parameters, and wherein the machine learning model is trained using data collected from a plurality of treatment sessions associated with a single user.

* * * * *